United States Patent [19]
Maurer et al.

[11] 4,251,529
[45] Feb. 17, 1981

[54] ERGOT PEPTIDE ALKALOIDS

[75] Inventors: Gerard Maurer, Ruelisheim; Jean-Rene Kiechel, Huningue, both of France

[73] Assignee: Sandoz Ltd., Basel, Switzerland

[21] Appl. No.: 119,877

[22] Filed: Feb. 8, 1980

Related U.S. Application Data

[63] Continuation of Ser. No. 50,750, Jun. 21, 1979, abandoned, which is a continuation of Ser. No. 951,951, Oct. 16, 1978, abandoned, which is a continuation of Ser. No. 878,563, Feb. 16, 1978, abandoned.

[30] Foreign Application Priority Data

Feb. 22, 1977 [CH] Switzerland ............... 2182/77

[51] Int. Cl.³ ............... A61K 31/495; C07D 519/02
[52] U.S. Cl. ............... 424/250; 544/346; 544/350
[58] Field of Search ............... 424/250; 544/346, 350

Primary Examiner—Mary C. Lee
Attorney, Agent, or Firm—Gerald D. Sharkin; Robert S. Honor; Thomas O. McGovern

[57] ABSTRACT

Compounds of formula I

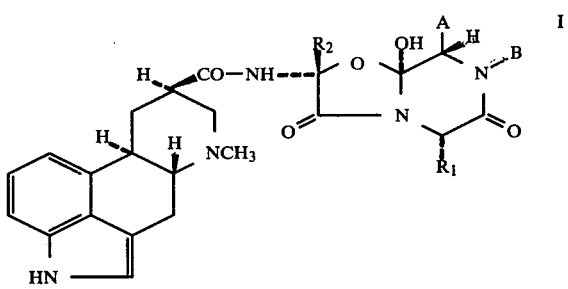

wherein
$R_1$ is alkyl of 1 to 4 carbon atoms or benzyl,
$R_2$ is alkyl of 1 to 4 carbon atoms, and
either
(i) A is $.CH_2.CH_2.COOH$; $.CH_2.CH(OH).COOH$ or $.CH(OH).CH_2.COOH$ and B is hydrogen, or (ii) A and B together are $.CH_2.CH(OH).CH_2.$; $CH_2.CH_2.CH(OH)$; $.CH_2.CH(OH).CH(OH).$ or $.CH(OH).CH_2.CH(OH).$ are useful cerebral insufficiency agents.

31 Claims, No Drawings

ERGOT PEPTIDE ALKALOIDS

This is a continuation, of application Ser. No. 50,750, filed June 21, 1979, now abandoned, which in turn is a continuation, of application Ser. No. 951,951, filed Oct. 16, 1978, now abandoned, which in turn is a continuation, of application Ser. No. 878,563, filed Feb. 16, 1978, now abandoned.

This invention relates to ergot peptide alkaloids.

According to the invention there is provided a compound of formula I

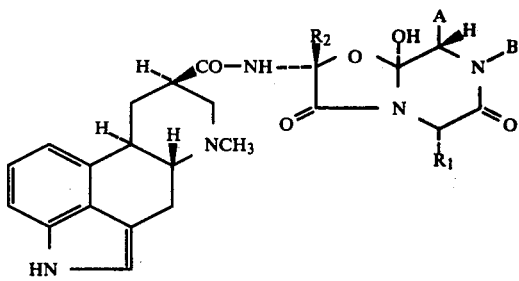

wherein
$R_1$ is alkyl of 1 to 4 carbon atoms or benzyl,
$R_2$ is alkyl of 1 to 4 carbon atoms, and
either
(i) A is .CH$_2$.CH$_2$.COOH; .CH$_2$.CH(OH).COOH or .CH(OH).CH$_2$.COOH and B is hydrogen, or (ii) A and B together are .CH$_2$.CH(OH).CH$_2$.; .CH$_2$.CH$_2$.CH(OH).; .CH$_2$.CH(OH).CH(OH). or .CH(OH).CH$_2$.CH(OH)..

It has now been found that basic members of formula I, e.g. when $R_1$ = isopropyl, iso-butyl, sec-butyl or benzyl, $R_2$ is isopropyl, and either (i) A is .CH$_2$.CH$_2$.COOH; .CH$_2$.CH(OH).COOH or .CH(OH).CH$_2$.COOH and B is hydrogen, or (ii) A and B together are .CH$_2$.CH($\beta$-OH).CH$_2$.; .CH$_2$.CH$_2$.CH(OH).; .CH$_2$.CH(OH).CH(OH). or .CH($\beta$-OH). CH$_2$.CH($\alpha$-OH).; .CH($\alpha$-OH).CH$_2$.CH($\beta$-OH), may be obtained by administering the corresponding 5′$\alpha$-alkyl (C$_{1-4}$)-, or benzyl-, 2′$\beta$-alkyl-12′$\alpha$-hydroxy-9,10-dihydroergopeptine to bile fistula rats, concentrating and purifying the bile extract, and isolating the compound of formula I therefrom e.g. as described in the Example 6 hereinafter.

Conveniently A is .CH$_2$.CH$_2$.COOH and B is H or A and B together are .CH$_2$.CH$_2$.CH(OH). or .CH$_2$.CH(OH).CH(OH).. Preferably, however, A or A and B contains one hydroxy group, e.g. —CH$_2$.CH($\beta$OH).CH$_2$.. When $R_1$ is alkyl this is preferably propyl or butyl, e.g. isopropyl, isobutyl or sec-butyl.

$R_2$ is for example methyl, ethyl or conveniently isopropyl.

The present invention also provides a synthetic compound of formula I which may be obtained e.g. by condensing a reactive functional acid derivative of dihydrolysergic acid with an acid addition salt of an aminocyclol of formula II

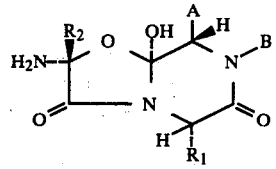

wherein A, B, $R_1$ and $R_2$ are as defined above.

The process may be effected in conventional manner for an analogous condensation reactions to prepare analogous ergot peptide alkaloids. When A or A and B contains a hydroxy group the preferred reactive functional acid derivative is the acid chloride hydrochloride. Alternative derivatives, e.g. when A or A and B contains no hydroxy group, include the mixed anhydride of this acid with trifluoroacetic acid, or the acid chloride reaction product of this acid with oxalyl chloride and dimethylformamide.

A suitable acid addition salt of an aminocyclol of formula II is the hydrochloride. Preferred reaction temperatures are from —30° to 0° C.

A compound of formula II may be synthesized from a compound of formula III

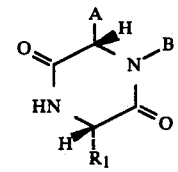

in conventional manner for the synthesis of an aminocyclol, e.g. by condensing with S-alkyl (C$_{1-4}$)-benzyloxymalonic acid mono ethyl ester acid chloride and subsequent hydrogenolysis in the presence of acid to give a compound of formula IV

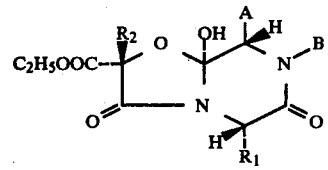

This compound of formula IV may be converted into a compound of formula II in conventional manner, e.g. via the corresponding 2-benzyloxycarbonyl aminocyclol as described in Example 1 hereinafter.

A compound of formula III may be prepared in conventional manner for the preparation of a diketopiperazine peptide, e.g. as described in Example 1 hereinafter.

If desired in any reaction step any hydroxy group or groups present may be temporarily protected, e.g. when one reaction partner contains a group that may react with a hydroxy group e.g. in the condensation step with a reactive functional acid derivative of dihydrolysergic acid or in the condensation step using the malonic acid chloride. For example a hydroxy group present may be protected as an acetyl ester. Two neighbouring hydroxy groups may be protec as a ketal, e.g. formed from acetone.

To prepare compounds wherein A and B together are a group .CH$_2$.CH$_2$CH(OH). or .CH$_2$.CH(OH). CH(OH). or .CH(OH).CH$_2$.CH(OH). an appropriate compound, wherein A is respectively .CH$_2$.CH$_2$.COOH or .CH$_2$.CH(OH).COOH, or .CH(OH).CH$_2$.COOH e.g. a compound of formula II wherein the 2-amino group is protected by benzyloxycarbonyl, may be used and a 2-oxo-pyrrolidine ring moiety may be formed by intramolecular condensation in analgous manner to that described in example 3B, using a cyclizing agent, followed by sodium borohydride reduction of the pyrrolidine keto group and separation of the resultant α and β hydroxy isomers. If desired the carboxyl group may be temporarily protected, e.g. as an alkyl (C$_{1-4}$) ester.

In so far as the production of any particular starting material is not particularly described then this is known or may be produced in conventional manner, e.g. for the preparation of peptides.

In particular a 2-benzyloxycarbonyl aminocyclol wherein A and B together are .CH$_2$.CH(OH).CH(OH). may be produced by splitting off water from a corresponding aminocyclol wherein A and B together are .CH$_2$.CH(OH).CH$_2$. in the presence of POCl$_3$ and pyridine, or splitting off methanesulphonic acid from the 9 mesylate of such an aminocyclol in the presence of pyridine, and reacting the resultant product with osmium tetroxide.

Free base forms of the compounds of formula I may be converted into acid addition salts, e.g. with methanesulphonic acid or tartaric acid, in conventional manner and vice versa.

By means of the above processes it is possible to prepare a compound of formula I in pure form, e.g. greater than 95% pure or greater than 98% pure. It is also possible to prepare a compound of formula I free form other ergot peptide alkaloids, or in crystalline form.

In the following examples all temperatures are in degrees centigrade and are uncorrected. All ratios refer to parts by volume except where otherwise stated.

Nomenclature: it is to be appreciated that when B is H in formula I the carbon atom to which A is attached is number 8 and the hydroxy group in formula I is attached to carbon atom number 9. Otherwise A is attached to carbon atom number 11 and the hydroxy group in formula I is attached to carbon atom number 12.

Thin layer chromatography is effected on Merck F$_{254}$ silicagel plates except where stated otherwise using the following solvent systems:

| System A: | CHCl$_3$/CH$_3$OH/water/25% aqueous NH$_4$OH 80/23/1.5/2 | |
|---|---|---|
| System B: | CHCl$_3$/CH$_3$OH | 90/10 |
| System C: | n-C$_3$H$_7$OH/NH$_3$/H$_2$O | 80/10/10 (on silicagel G 0.2 mm) |
| System D: | CH$_2$Cl$_2$/CH$_3$OH | 97/3 (on silicagel MN-GHR 0.5mm) |
| System E: | CH$_2$Cl$_2$/CH$_3$OH | 90/10 (silicagel G 0.2 mm) |

N.M.R. Spectra refer to characteristic peaks only. All the final compounds of formula I are obtained in greater than 95% purity (by weight).

EXAMPLE 1:

9'β-hydroxy-9,10-dihydro-β-ergocryptine

Method A (Direct condensation)

1.7 g (2R, 5S, 9R, 11S, 12S) 2-amino-5-secbutyl-9,12-dihydroxy-3,6-dioxo-2-isopropyloctahydro-8H- oxazolo[3,2-a]pyrrolo[2,1-c]pyrazine hydrochloride and 2.16 g 9,10-dihydrolysergic acid chloride hydrochloride are suspended in 40 ml absolute methylene chloride. The mixture is cooled to 0° and 22 ml of absolute pyridine are added. The mixture is stirred for ½ hour at 0°, warmed to 20° and stirred for 1 hour. The mixture is worked up in conventional manner to give the title compound in free base form after chromatography on silicagel.

N.M.R. (90 MHz (Pyridine-d$_5$) 11.53 (s, 1H); 9.96 (s, 1H); 8.38 (d, J=2, 1H); 6.8–7.2 (m, 4H); 4.91 (d, J=3, 1H); 0.9–1.6 (m, 12H).

The aminocyclol starting material may be obtained as follows:

(a) A solution of 1.6 g L-benzyloxycarbonylisoleucine and 1 g L-4-hydroxyproline n-butyl ester in 8 ml methylene chloride and 3 ml ether are treated with a solution of 1.3 g dicyclohexyl carbodiimide in ether. The mixture is stirred for 2 hours at room temperature and after 0.3 ml of 50% acetic acid are added stirred for another hour. The mixture is filtered, washed with ice cold 2 N HCl and then ice cold sodium bicarbonate, dried over sodium sulphate and evaporated. Chromatography of the residue on silicagel using CH$_2$Cl$_2$+1%CH$_3$OH as eluant yields L-carbobenzoxyisoleucine-L-4-hydroxyproline n-butyl ester which is hydrogenated in 13 ml ethyl acetate in the presence of 0.23 g palladium-on-charcoal (10% w/w). Filtration and evaporation yield (3S, 7R, 8aS)-3-sec-butyl-7-hydroxy-1,4-dioxo-octahydropyrrolo[1,2-a]pyrazine. M.pt 156° (decomp).

(b) 22 g of (3S, 7R, 8aS)-3-sec-butyl-7-hydroxy-1,4-dioxo-octahydropyrrolo[1,2-a]pyrazine is converted into the acetyl derivative by reacting with 110 ml acetic anhydride in 110 ml pyridine at 0° to 20° over 5 hours.

11 g of the acetyl derivative in 90 ml chloroform are treated with 3.6 ml absolute pyridine and 13.8 g S-(+)-isopropyl-benzyloxymalonic acid monoethyl ester acid chloride. The mixture is stirred at 61° for 20 hours. Working up in conventional manner gives (3S, 7R, 8aS) 7-acetoxy-3-secbutyl-2-(α-ethoxycarbonyl-α-benzyloxy-β-methylbutyryl)-1,4-dioxo-octahydropyrrolo[1,2-a]pyrazine as an oil.

(c) 19.8 g of the product obtained in step (b) in 300 ml ethanol, 20 ml methylene chloride and 21.8 ml 2 N sulphuric acid in the presence of 2 g palladium on charcoal (10% w/w) are hydrogenated. Working up gives (2R, 5S, 9R, 11S, 12S) 9-acetoxy-5-sec-butyl-2-ethoxycarbonyl-12-hydroxy-3,6-dioxo-2-isopropyl-octahydro-8H-oxazolo[3,2-a]pyrrolo[2,1-c]pyrazine.

(d) 15 g of the product obtained in step (c) in 540 ml methanol are treated at 0° with 4.92 ml hydrazine hydrate and stirred for 5 hours. The solution is diluted with 2.16 liters methylene chloride, filtered through 150 g silicagel and chromatographed to give (2R, 5S, 9R, 11S, 12S) 9-acetoxy-5-sec-butyl-2-hydrazinocarbonyl-12-hydroxy-3,6-dioxo-2-isopropyloctahydro-8H-oxazolo[3,2-a]pyrrolo[2,1-c]pyrazine.

(e) 3 g of the product obtained in step (d) in 135 ml methanol are treated with 3.8 ml 2 N potassium hydroxide in methanol at room temperature and maintained for ½ hour at room temperature. Working up gives (2R, 5S, 9R, 11S, 12S)-5-sec-butyl-2-hydrazinocarbonyl-9,12-dihydroxy-3,6-dioxo-2-isopropyl-octahydro-8H-oxazolo[3,2-a]pyrrolo[2,1-c]pyrazine.

(f) 5 g of the product obtained in step (e) in 23.5 ml chloroform are added to 23 ml 2 N sulphuric acid at 0°.

Over 10 minutes 2.4 ml of 5 N sodium nitrite solution are added. After 45 minutes stirring at 0° the mixture is treated with solid potassium bicarbonate until the pH is 3. The organic phase is separated, dried with sodium sulphate and filtered. The filtrate is treated with 3 drops of concentrated hydrochloric acid and 2.4 ml benzyl alcohol, and boiled for 2 hours. After cooling to room temperature, the mixture is shaken with ice cold potassium bicarbonate solution, dried over sodium sulphate, filtered and evaporated to yield after chromatography (2R, 5S, 9R, 11S, 12S) 2-benzyloxycarbonylamino-5-sec-butyl-9,12-dihydroxy-3,6-dioxo-2-isopropyl-octahydro-8H-oxazolo[3,2-a]pyrrolo[2,1-c]pyrazine.

(g) 3.9 g of the product obtained in step (f) in 80 ml anhydrous tetrahydrofuran are treated with 5.76 ml 1.6 N ethereal hydrogen chloride and 2 g palladium on charcoal (10% w/w) are added. Hydrogeration and working up yields (2R, 5S, 9R, 11S, 12S)-2-amino-5-sec-butyl-9,12-dihydroxy-3,6-dioxo-2-isopropyloctahydro-8H-oxazolo[3,2-a]pyrrolo[2,1-c]pyrazine. hydrochloride.

Method B (Temporary hydroxy protection using acetyl group)

2.16 g of 9,10-dihydrolysergic acid (dried in a high vacuum) suspended in 16 ml dimethylformamide and 8 ml absolute acetonitrile are treated with 8 ml trifluoroacetic acid. After cooling to −10° C. the mixture is treated with 1.12 ml trifluoroacetic acid anhydride and 16 ml absolute pyridine and stirred for 15 minutes at −10°. 1.7 g (2R, 5S, 9R, 11S, 12S)-9-acetoxy-2-amino-5-sec-butyl-12-hydroxy-3,6-dioxo-2-isopropyl-octahydro-8H-oxazolo[3,2-a]pyrrolo[2,1-c]pyrazine hydrochloride [prepared in analogous manner to the aminocyclol starting material of the above Method A without the step of paragraph (e)] are added.

The mixture is allowed to warm up over ½ hour to 0° and stirred for ½ hour at 0° and a further ½ hour at room temperature. The mixture is worked up in conventional manner to give the 9'-acetyl derivative of the title compound in free base form, which is selectively hydrolysed using 2 N potassium hydroxide in methanol at room temperature for ½ hour followed by isolation and chromatographic purification to give the title compound.

EXAMPLE 2: 6-methyl-N[(2′R, 5′S′, 8′S, 9′S)-5′-sec-butyl-9′-hydroxy-3′,6′-dioxo-8′-(2″-carboxyethyl)-hexahydro-7′H-2′-isopropyloxazolo[3,2-a]pyrazin-2′-yl]ergolin-8β-carboxamide

[Compound of formula I wherein A is .CH$_2$.CH$_2$.COOH and B is H]

Method A (Direct condensation)

The method A of example I is used using as the aminocyclol (2R, 5S, 8S, 9S) 2-amino-5-sec-butyl-9-hydroxy-3,6-dioxo-2-isopropyl-8-(2′carboxyethyl)-hexahydro-7H-oxazolo[3,2-a]pyrazine hydrochloride (which may be obtained from 2S, 5S-sec-butyl-3,6-dioxo-piperazine-2-propionic acid as the compound of formula III). The title compound in free form has M.pt. 170° (decomp.).

Method B (Temporary protection as methyl ester)

450 ml absolute dimethylformamide at −15° are treated dropwise with 9.48 ml oxalyl chloride in 40 ml absolute acetonitrile. 29.7 g dry dihydrolysergic acid are added. The mixture is stirred for ½ hour at 0°, with strong cooling whilst 18 ml absolute pyridine and 25 g of the methyl ester of the aminocyclol used in method A immediately above are added. The methyl ester of the title compound thereby formed [N.M.R. 3.65 (s,3H)] is selectively hydrolysed in analogous manner to Example I Method B to give the title compound.

EXAMPLE 3: 8′α and 8′β-hydroxy-9,10-dihydro-β-ergocryptine

Method A (Direct condensation)

The compounds may be obtained in analogous manner to that described in Example I Method A using as the aminocyclol (2R, 5S, 8R or S, 11S, 12S) 2-amino-5-sec-butyl-8,12-dihydroxy-3,6-dioxo-2-isopropyl-octahydro-8H-oxazolo[3,2-a]pyrrolo[2,1-c]pyrazine hydrochloride. On thin layer chromatography on silica gel eluting with chloroform/methanol (90/10) Rf of 8′αisomer=0.43. Rf of 8′β isomer=0.46.

Method B (Interconversion)

7.3 g of the title compound of Example 2 in 120 ml absolute acetonitrile and 60 ml absolute dimethylformamide are treated with 3.4 ml acetic anhydride and 4.0 ml absolute pyridine. The mixture is warmed to 80° for 30 minutes to produce 8′-oxo-9,10-dihydro-β-ergocryptine which is reduced with 4.5 g sodium borohydride at −40° in 300 ml absolute dimethylformamide/absolute ethanol 2:1 over 4½ hours. The mixture is worked up to give the two title compounds which are separated on thin layer chromatography.

EXAMPLE 4

In analogous manner to that described in Example I Method A the following compounds of formula I may be obtained, wherein R$_2$ is isopropyl and:

| R$_1$ | A | B Physical characteristics |
|---|---|---|
| (a) sec-butyl | —(R)CH(OH) . CH$_2$ . COOH | H Rf 0.1 System A |
| (b) sec-butyl | —(S)CH(OH) . CH$_2$ . COOH | H Rf 0.1 System A |
| (c) sec-butyl | —(R)CH$_2$ . CH(OH) . COOH | H Rf 0.13 System A |
| (d) sec-butyl | —(S)CH$_2$ . CH(OH) . COOH | H Rf 0.13 System A |
| (e) benzyl | . CH$_2$ . CH$_2$ . COOH | H Rf 0.13 System A |
| (f) iso-butyl | . CH$_2$ . CH$_2$ . COOH | H Rf 0.55 System C |
| (g) iso-propyl | .CH$_2$ . CH$_2$ . COOH | H Rf 0.24 System E |

EXAMPLE 5

In analogous manner to that described in Example I Method A the following compounds may be obtained (Rf values and solvent systems in brackets):

(a)  8′β,9′α-dihydroxy-9,10-dihydro-β-ergocryptine (0.27;B)
(b)  8′α,]′α-dihydroxy-9,10-dihydro-β-ergocryptine (0.25;B)
(c)  8′α,9′β-dihydroxy-9,10-dihydro-β-ergocryptine (0.23;B)
(d)  8′β,9′β-dihydroxy-9,10-dihydro-β-ergocryptine (0.25;B)
(e)  8′α,10′β-dihydroxy-9,10-dihydro-β-ergocryptine (0.06;B)

(f) 8'β,10'α-dihydroxy-9,10-dihydro-β-erogcryptine (0.06;B)
(g) 8'α-hydroxy-9,10-dihydro-α-ergocryptine (0.18;D)
(h) 8'β-hydroxy-9,10-dihydro-α-ergocryptine (0.18;D)
(i) 8'α,9'α-dihydroxy-9,10-dihydro-α-ergocryptine (0.31;E)
(j) 8'α,9'β-dihydroxy-9,10-dihydro-α-ergocryptine (0.31;B)
(k) 8'β,9'β-dihydroxy-9,10-dihydro-α-ergocryptine (0.31;E)
(l) 8'β,9'α-dihydroxy-9,10-dihydro-α-ergocryptine (0.31;E)

EXAMPLE 6: Administration of 9,10-dihydro-β-ergocryptine to rats (a) Administration 1 ml of a 5% (w/w) glucose solution containing 10 mg of 9,10-dihydro-β-ergocryptine mesylate per ml is administered i.p. 3 times daily to 18 male Wistar bile fistula rats. The bile of the rats was collected in tubes cooled in dry ice and stored at −20°. The bile collected over 5 weeks was lyophilized.

(b) First Chromatography 200 g of an appropriate resin copolymer of styrene and divinylbenzene, e.g. Amberlite XAD-2 (50–100μ particle diameter) was washed for 4 hours with methanol. The resin is filtered and the small particles removed. The process is repeated until all small particles have been removed. The resin is treated with water/methanol 9:1 to produce a liquid gel which is filled into a Cheminert column (height 40 cm, diameter 2.5 cm). After sedimentation of the resin a solution of 2 g of the lyophilized bile in 10 g water is added to the column. Elution is carried out starting with water/methanol 9:1 and increasing the methanol content to 100% over 160 fractions of 24 ml/fraction. Elution rate 120 ml/hour. The fractions are monitored according to their absorption at 280 nm. Absorbent fractions are as follows: Group I—Eluant H$_2$O/CH$_3$OH 45/55 to 40/60-fraction Nos 82–91; Group II—Eluant H$_2$O/CH$_3$OH 40/60 to 25/75-fractions Nos 92 to 114; Group III—Eluant H$_2$O/CH$_3$OH 25/75 to 0/100-fraction Nos 115 to 142.

(c) Second Chromatography

Group I fractions

These are evaporated. The residue is taken up in 0.05 M NH$_4$HCO$_3$ and applied to an ion-exchange column [Sephadex DEAE A-25 particle diameter 40–100μ; column height 42 cm, diameter 2.5 cm] previously equilibrated with 0.05 M NH$_4$HCO$_3$. Elution is carried out starting with 0.05 M NH$_4$HCO$_3$ rising to 1 M NH$_4$HCO$_3$ over 200 fractions of 24 ml. Elution rate 120 ml/hour. There are eluted in fractions 100 to 120 a compound or compound mixture of formula I wherein R$_1$ is secbutyl, R$_2$ is isopropyl and A is R-and/or S-CH(OH).CH$_2$. COOH; and in fractions 121 to 140 a compound or compound mixture of formula I wherein R$_1$ is sec-butyl, R$_2$ is isopropyl and A is R-and/or S-CH$_2$.CH(OH).COOH.

Group II fractions

In analogous manner to the Group I fractions, the Group II fractions are chromatographed starting with 0.05 M NH$_4$HCO$_3$ rising to 1M NH$_4$HCO$_3$ over 300 fractions of 24 ml at an elution rate of 300 ml/hour to elute the title compound of Example 2.

Group III fractions

These are evaporated. The residue is taken up in CHCl$_3$/CH$_3$OH (98/2) and applied to a silicagel filter (Merck; silicagel 60 particle size 0.023–0.040 mm). The filter is first washed with 500 ml of chloroform and the filtrate is rejected. It is subsequently washed with chloroform/methanol (90/10). The latter filtrate is placed on a silica column (Merck prepacked column: size B), which has previously been equilibriated with a mixture of chloroform saturated with water/methanol 6%. The column is eluted with a gradient of chloroform saturated with water, containing from 6 to 9% methanol. (rate 120 ml/hour; 120 fractions of 15 ml).

The following u.v. absorbant (280 nm) fractions are combined; fractions 12 to 22 (C); 23 to 31 (D); 32 to 39 (E); 40 to 44 (F); 45 to 52 (G); and 53 to 60 (H); and purified on a silicagel column (Merck; Lichrosorb SI 60 5 μ) which is prepared as follows: 7 g of silica Lichrosorb SI 60 5μ;0 are added to 40 ml of ether and placed for 20 minutes in an ultrasonic bath. The suspension is subsequently placed in a glass column (0.9 cm×100 cm) and the solvent is pumped through the column (20 ml/min, 700 psi). The column thus obtained (0.9×16 cm) is equilibriated for 8 hours with chloroform saturated in water (2 ml/min).

The above fractions are eluted with the following solvent mixtures; from the Lichrosorb column:

| C with CHCl$_3$/CH$_3$OH | 3% |
| D with CHCl$_3$/CH$_3$OH | 4% |
| E with CHCl$_3$/CH$_3$OH | 6% |
| F with CHCl$_3$/CH$_3$OH | 6% |
| G with CHCl$_3$/CH$_3$OH | 6% |
| H with CHCl$_3$/CH$_3$OH | 7% |

Fractions C are then subjected to silica gel thin layer chromatography to yield 8'α-hydroxy-9,10-dihydro-β-ergocryptine and 8'β-hydroxy-9,10-dihydro-β-ergocryptine using CHCl$_3$/CH$_3$OH 90/10 as eluant. Fractions D, E and G on simlar silicagel thin layer chromatography yield respectively, 8'β',9α-; 8'α,9'α- and 8'α,9'β-dihydroxy-9,10dihydro-β-ergocryptines. Fraction F on analogous chromatography yields 9'β-hydroxy-9,10-dihydro-β-ergocryptine. Fraction H yields on thin layer chromatography 8'β,10'α- and 8'α,10'β-dihydroxy-9,10-dihydro-β-ergocryptines.

In analogous manner the following compounds may also be administered to rats and compounds of formula I may be isolated from the bile extract.

(a) 9,10-dihydro-α-ergocryptine may be administered and there may be isolated, inter alia, a compound of formula I wherein A is CH$_2$.CH$_2$.COOH and B is H and R$_1$ is isobutyl and R$_2$ is isopropyl as well as 8'-hydroxy-9,10-dihydro-α-ergocryptine (isomer mixture) and 8',9'-dihydroxy-9,10-dihydro-α-ergocryptine (isomer mixture).

(b) 9,10-dihydro-ergocornine may be administered and there may be isolated, inter alia, a compound of formula I wherein A is CH$_2$.CH$_2$.COOH and B is H and R$_1$ is isopropyl and R$_2$ is isopropyl.

(c) 9,10-dihydro-ergocristine may be administered and there may be isolated, inter alia, a compound of formula I wherein A is CH$_2$.CH$_2$.COOH and B is H and R$_1$ is benzyl and R$_2$ is isopropyl.

The compounds of formula I are useful because they possess pharmacological activity in animals. In particular, the compounds of formula I are useful as vigilance increasing agents, e.g. for the treatment of cerebral insufficiency, as indicated by a prolongation of the wake phase and a decrease of the sleep phases, e.g. of classical sleep and of paradoxical sleep and a prolongation of the latency period up to the first appearance of paradoxical sleep on i.p. administration of 1 to 3 mg/kg to a rat having EEG electrodes chronically implanted in its brain. Additionally, when the compound is administered at a dose of from 0.1 to 0.6 mg/kg i.v. to a cat previously administered with reserpine, the frequency of P.G.O. peaks on the "corpus geniculatum laterale" is reduced. The above test methods are described e.g. in H. Depoortere and D. Loew, The nature of sleep international symposium pp. 101–104 (Fischer, Stuttgart 1973) and H. Depoortere 1st Europ.Congr. Sleep Research Basel 1972 pp. 360–364 (Karger, Basle, 1973). For the above mentioned use the dosage will, of course, vary depending on the compounds employed, mode of administration and therapy desired. However, in general, satisfactory results are obtained when administered at a daily dosage of from 0.1 mg to about 10 mg per kg animal body weight, conveniently given in divided doses 2 to 4 times a day or in sustained release form.

For the larger mammal, the total daily dosage is in the range from about 5 to about 60 mg, and dosage forms suitable for oral administration comprise from about 1.5 mg to about 30 mg of the compound admixed with a solid or liquid pharmaceutical carrier or diluent.

The compounds of formula I may be administered in pharmaceutically acceptable acid addition salt form. Such acid addition salt forms exhibit the same order of activity as the free base forms. The present invention also provides a compound of formula I in pharmaceutically acceptable form, such as in sterile form, and especially a pharmaceutical composition comprising a compound of formula I, in free base form or in pharmaceutically acceptable acid addition salt form, in association with a pharmaceutical carrier or diluent. Such compositions may be in the form of, for example, a solution, a dragee, a capsule; granules, a powder or a tablet, and especially a sterile solution for i.p. administration.

For example, liquid pharmaceutical compositions may be in sealed unit dosage forms and contain a compound of formula I in a concentration acceptable for liquid pharmaceutical compositions in the ergot art e.g. greater than 0.1 mg/ml, such as 0.1 to 5 mg/ml.

In a first group of compounds A is .CH(OH).CH$_2$.COOH and B is H. In a second group A is .CH$_2$CH(OH).COOH and B is H. In a third group A and B together are .CH$_2$CH(OH).CH$_2$.; .CH(OH).CH$_2$.CH(OH). or .CH(OH).CH$_2$.CH$_2$. In fourth group A and B are .CH$_2$.CH($\beta$-OH).CH$_2$.; .CH($\beta$-OH).CH$_2$.CH($\alpha$-OH).; CH($\alpha$-OH).CH$_2$.CH($\beta$-OH). or .CH(OH).CH$_2$.CH$_2$.. In a fifth group A is .CH$_2$.CH$_2$.COOH and B is H. In a sixth group A and B are together CH$_2$.CH($\alpha$-OH).CH$_2$.; .CH($\alpha$-OH).CH$_2$.CH($\alpha$-OH)., or .CH($\beta$-OH).CH$_2$.CH($\beta$-OH). In a sub-group of each of those five groups R$_2$ is isopropyl.

We claim:
1. A compound of formula I

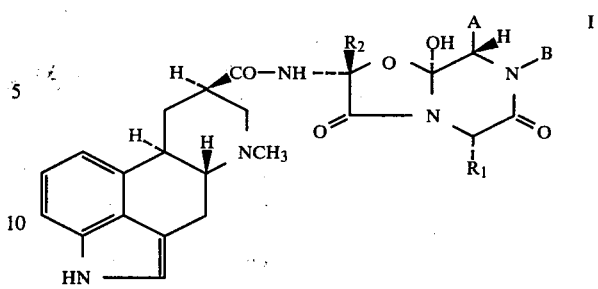

wherein
R$_1$ is alkyl of 1 to 4 carbon atoms or benzyl,
R$_2$ is alkyl of 1 to 4 carbon atoms, and
either
(i) A is .CH$_2$.CH$_2$.COOH; .CH$_2$.CH(OH).COOH or .CH(OH).CH$_2$.COOH and B is hydrogen, or (ii) A and B together are .CH$_2$.CH(OH).CH$_2$.; .CH$_2$.CH$_2$.CH(OH); .CH$_2$CH(OH).CH(OH). or .CH(OH).CH$_2$.CH(OH). or a pharmaceutically acceptable acid addition salt thereof.

2. A method of treating cerebral insufficiency in animals which comprises administering to an animal in need of such treatment a therapeutically effective amount of a compound of claim 1.

3. A pharmaceutical composition comprising a compound of formula I claim 1 in pharmaceutically acceptable form in association with a pharmaceutical carrier or diluent.

4. A compound of claim 1 in pure form.

5. A compound of claim 1, which is greater than 95% pure.

6. A compound of claim 4, in which A and B together are .CH$_2$.CH(OH).CH$_2$.; .CH(OH).CH$_2$.CH(OH). or .CH(OH).CH$_2$.CH$_2$..

7. A compound of claim 4, in which A and B together are .CH$_2$.CH($\beta$-OH).CH$_2$.; .CH($\beta$-OH).CH$_2$.CH($\alpha$-OH).; .CH($\alpha$-OH).CH$_2$.CH($\beta$-OH). or CH(OH).CH$_2$.CH$_2$.

8. A compound of claim 4, in which A and B together are .CH$_2$.CH($\alpha$-OH).CH$_2$; .CH($\alpha$-OH).CH$_2$.CH($\alpha$-OH). or .CH($\beta$-OH). CH$_2$.CH($\beta$-OH).

9. The compound of claim 4, which is 9'$\beta$-hydroxy-9,10-dihydro-$\beta$-ergocryptine.

10. The compound of claim 4, which is 6-methyl-N [(2'R, 5'S', 8'S, 9'S)-5'-sec-butyl-9'-hydroxy-3',6'-dioxo-8'-(2''-carboxyethyl)-hexahydro-7'H-2'-isopropyl-oxazolo[3,2-a]pyrazin-2'-yl]ergolin-8$\beta$-carboxamide.

11. The compound of claim 4, which is 8'$\alpha$ or 8'$\beta$-hydroxy-9,10-dihydro-$\beta$-ergocryptine.

12. The compound of claim 4, wherein R$_2$ is isopropyl and R$_1$, A and B are respectively sec-butyl, —(R)C-H(OH)—CH$_2$—COOH and H.

13. The compound of claim 4, wherein R$_2$ is isopropyl and R$_1$, A and B are respectively sec-butyl, —(S)C-H(OH)—CH$_2$—COOH and H.

14. The compound of claim 4, wherein R$_2$ is isopropyl and R$_1$, A and B are respectively sec-butyl, —(R)C-H$_2$—CH(OH)—COOH and H.

15. The compound of claim 4, wherein R$_2$ is isopropyl and R$_1$, A and B are respectively sec-butyl, —(S)C-H$_2$—CH(OH)—COOH and H.

16. The compound of claim 4, wherein R$_2$ is isopropyl and R$_1$, A and B are respectively benzyl, —CH$_2$—CH$_2$—COOH and H.

17. The compound of claim 4, wherein $R_2$ is isopropyl and $R_1$, A and B are respectively iso-butyl, —CH$_2$—CH$_2$—COOH and H.

18. The compound of claim 4, wherein $R_2$ is isopropyl and $R_1$, A and B are respectively iso-propyl, —CH$_2$—CH$_2$—COOH and H.

19. The compound of claim 4, which is 8'β, 9'α-dihydroxy-9,10-dihydro-β-ergocryptine.

20. The compound of claim 4, which is 8'α, 9'α-dihydroxy-9,10-dihydro-β-ergocryptine.

21. The compound of claim 4, which is 8'α, 9'β-dihydroxy-9,10-dihydro-β-ergocryptine.

22. The compound of claim 4, which is 8'β, 9'β-dihydroxy-9,10-dihydro-β-ergocryptine.

23. The compound of claim 4, which is 8'α, 10'β-dihydroxy-9,10-dihydro-β-ergocryptine.

24. The compound of claim 4, which is 8'β, 10'α-dihydroxy-9,10-dihydro-β-ergocryptine.

25. The compound of claim 4, which is 8'α-hydroxy-9,10-dihydro-α-ergocryptine.

26. The compound of claim 4, which is 8'β-hydroxy-9,10-dihydro-α-ergocryptine.

27. The compound of claim 4, which is 8'α, 9'α-dihydroxy-9,10-dihydro-α-ergocryptine.

28. The compound of claim 4, which is 8'α, 9'β-dihydroxy-9,10-dihydro-α-ergocryptine.

29. The compound of claim 4, which is 8'α, 9'β-dihydroxy-9,10-dihydro-α-ergocryptine.

30. The compound of claim 4, which is 8'β, 9'α-dihydroxy-9,10-dihydro-α-ergocryptine.

31. The compound of claim 4 in which A and B together are .CH$_2$.CH(β-OH).CH$_2$.

* * * * *